US012762704B2

(12) United States Patent
Banerjee et al.

(10) Patent No.: US 12,762,704 B2
(45) Date of Patent: Oct. 13, 2026

(54) SYSTEM AND METHOD FOR ONE-SHOT AUTOMATIC TI PREDICTION FOR CARDIAC MRI

(71) Applicant: GE Precision Healthcare LLC, Waukesha, WI (US)

(72) Inventors: Subhashis Banerjee, Kolkata (IN); Sudhanya Chatterjee, Bangalore (IN); Dattesh Dayanand Shanbhag, Bangalore (IN)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 156 days.

(21) Appl. No.: 19/007,893

(22) Filed: Jan. 2, 2025

(65) Prior Publication Data

US 2026/0187802 A1 Jul. 2, 2026

(51) Int. Cl.
*G06T 7/00* (2017.01)
*A61B 5/00* (2006.01)
(Continued)

(52) U.S. Cl.
CPC .......... *G06T 7/0016* (2013.01); *A61B 5/0044* (2013.01); *A61B 5/055* (2013.01);
(Continued)

(58) Field of Classification Search
CPC . G06T 7/0016; G06T 7/11; G06T 7/73; G06T 2207/10088; G06T 2207/20084;
(Continued)

(56) References Cited

U.S. PATENT DOCUMENTS

| | | | | |
|---|---|---|---|---|
| 10,909,681 B2 | 2/2021 | Hsiao et al. | | |
| 2010/0085051 A1* | 4/2010 | Littmann | ............... | A61B 5/055 324/309 |
| 2025/0147136 A1* | 5/2025 | Chitiboi | .................... | G06T 7/11 |

FOREIGN PATENT DOCUMENTS

WO WO 2005/043467 A2 * 12/2005 ............ G06T 15/00

OTHER PUBLICATIONS

Yoon et al., "Validation of a Deep Learning based Automated Myocardial Inversion Time Selection for Late Gadolinium Enhancement Imaging in a Prospective Study," Proc. Intl. Soc. Mag. Reson. Med., 2021, 3 pgs.

(Continued)

*Primary Examiner* — David F Dunphy
(74) *Attorney, Agent, or Firm* — Fletcher Yoder, P.C.

(57) ABSTRACT

A method includes utilizing a first trained neural network to localize a cardiac region in a TI-scout MIP image to generate a ROI segmentation mask for the cardiac region. The method also includes utilizing the ROI segmentation mask on the TI-scout MIP image and a series of MR scout temporal frames to generate a ROI cropped TI-scout MIP image and ROI cropped MR scout temporal frames, respectively. The method includes generating a distance score plot by computing a distance between each ROI cropped MR scout temporal frame and the ROI cropped TI-scout MIP image. The method includes analyzing the distance score plot to approximate a span of the MR scout temporal frames for optimal TI frame estimation and utilizing a second trained neural network to determine an optimal TI frame from the span of the MR scout temporal frames.

20 Claims, 12 Drawing Sheets

(51) Int. Cl.
*A61B 5/055* (2006.01)
*G06T 7/11* (2017.01)
*G06T 7/73* (2017.01)

(52) U.S. Cl.
CPC .................. *G06T 7/11* (2017.01); *G06T 7/73* (2017.01); *G06T 2207/10088* (2013.01); *G06T 2207/20084* (2013.01); *G06T 2207/20132* (2013.01); *G06T 2207/30048* (2013.01)

(58) Field of Classification Search
CPC . G06T 2207/20132; G06T 2207/30048; A61B 5/0044; A61B 5/055
See application file for complete search history.

(56) References Cited

OTHER PUBLICATIONS

Bahrami et al., "Automated selection of myocardial inversion time with a convolutional neural network: Spatial temporal ensemble myocardium inversion network (STEMI-NET)," Magnetic Resonance in Medicine, 2019, 9 pgs.

* cited by examiner

262

| | # Samples | Frame range |
|---|---|---|
| Test | 200 | (6,54) |
| Train | 1226 | (10,54) |

264

| Model | Accuracy | # params. |
|---|---|---|
| DAtt-3D CNN on ROI | 88.28 % ( ± 1 frames) | 267,705 |

FIG. 6

SYSTEM AND METHOD FOR ONE-SHOT AUTOMATIC TI PREDICTION FOR CARDIAC MRI

BACKGROUND

The subject matter disclosed herein relates to medical imaging and, more particularly, to a system and a method for one-shot automatic inversion time (TI) prediction for cardiac magnetic resonance imaging (MRI).

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

During MRI, when a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment, $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradient fields vary according to the particular localization method being used. The resulting set of received nuclear magnetic resonance (NMR) signals are digitized and processed to reconstruct the image using one of many well-known reconstruction techniques.

Delayed myocardium enhanced imaging post contrast is used for assessing various myocardium tissue pathologies. This imaging requires determination of the optimal inversion time (TI). This is determined using a TI-scout which acquires multiple frames with different inversion times and then optimal TI is determined using visual inspection or automation. The challenge presented on the practical front is that, depending on the site preference, the number of acquired frames may vary. With changing the number of frames, the contrasts presented by the frames also change. A common automated approach is to use a sliding window over the multiple time frames which utilize a deep learning-based approach to determine the optimal T1 frame. However, the optimal TI frame location can also vary based on patient conditions and contrast injection parameters. This would then require multiple passes of the sliding window to determine the optimal TI frame, which is not an efficient approach.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a computer-implemented method for determining an optimal inversion time (TI) is provided. The computer-implemented method includes obtaining, via a processing system comprising one or more processors, a series of magnetic resonance (MR) scout temporal frames of a subject from MR scout imaging data acquired with an MR scanner utilizing a TI-scout sequence. The computer-implemented method also includes obtaining a TI-scout maximum intensity projection (MIP) image from the MR scout imaging data. The computer-implemented method further includes utilizing, via the processing system, a first trained neural network to localize a cardiac region in the TI-scout MIP image to generate a region of interest (ROI) segmentation mask for the cardiac region. The computer-implemented method even further includes utilizing, via the processing system, the ROI segmentation mask on the TI-scout MIP image and the series of MR scout temporal frames to generate a ROI cropped TI-scout MIP image and ROI cropped MR scout temporal frames, respectively. The computer-implemented method yet further includes generating, via the processing system, a distance score plot by computing a distance between each ROI cropped MR scout temporal frame and the ROI cropped TI-scout MIP image. The computer-implemented method further includes automatically analyzing, via the processing system, the distance score plot to approximate a span of the MR scout temporal frames for optimal TI frame estimation, wherein the span of the MR scout temporal frames encompasses a transition region including phase changes in the cardiac region including blood pool nulling, remote myocardium nulling, and initial recovery. The computer-implemented method even further includes utilizing, via the processing system, a second trained neural network to determine an optimal TI frame from the span of the MR scout temporal frames, wherein determination of the optimal TI frame occurs in a single pass.

In another embodiment, a system for determining an optimal inversion time (TI) is provided. The system includes a memory encoding processor-executable routines. The system also includes a processing system including one or more processors and configured to access the memory and to execute the processor-executable routines, wherein the processor-executable routines, when executed by the processing system, cause the processing system to perform actions. The actions include obtaining a series of magnetic resonance (MR) scout temporal frames of a subject from MR scout imaging data acquired with an MR scanner utilizing a TI-scout sequence. The actions also include obtaining a TI-scout maximum intensity projection (MIP) image from the MR scout imaging data. The further include utilizing a first trained neural network to localize a cardiac region in the TI-scout MIP image to generate a region of interest (ROI) segmentation mask for the cardiac region. The actions even further include utilizing the ROI segmentation mask on the TI-scout MIP image and the series of MR scout temporal frames to generate a ROI cropped TI-scout MIP image and ROI cropped MR scout temporal frames, respectively. The actions still further include generating a distance score plot by computing a distance between each ROI cropped MR scout temporal frame and the ROI cropped TI-scout MIP image. The actions further include automatically analyzing the distance score plot to approximate a span of the MR scout temporal frames for optimal TI frame estimation, wherein the span of the MR scout temporal frames encompasses a transition region including phase changes in the cardiac region including blood-pool nulling, remote myocardium nulling, and initial recovery. The actions further include utilizing a second trained neural network to determine an optimal TI frame from the span of the MR scout temporal frames, wherein determination of the optimal TI frame occurs in a single pass.

In a further embodiment, a non-transitory computer-readable medium, the computer-readable medium including processor-executable code that when executed by a processing system including one or more processors, causes the processing system to perform actions. The actions include obtaining a series of magnetic resonance (MR) scout temporal frames of a subject from MR scout imaging data acquired with an MR scanner utilizing a TI-scout sequence. The actions also include obtaining a TI-scout maximum intensity projection (MIP) image from the MR scout imaging data. The further include utilizing a first trained neural network to localize a cardiac region in the TI-scout MIP image to generate a region of interest (ROI) segmentation mask for the cardiac region. The actions even further include utilizing the ROI segmentation mask on the TI-scout MIP image and the series of MR scout temporal frames to generate a ROI cropped TI-scout MIP image and ROI cropped MR scout temporal frames, respectively. The actions still further include generating a distance score plot by computing a distance between each ROI cropped MR scout temporal frame and the ROI cropped TI-scout MIP image. The actions further include automatically analyzing the distance score plot to approximate a span of the MR scout temporal frames for optimal TI frame estimation, wherein the span of the MR scout temporal frames encompasses a transition region including phase changes in the cardiac region including blood-pool nulling, remote myocardium nulling, and initial recovery. The actions further include utilizing a second trained neural network to determine an optimal TI frame from the span of the MR scout temporal frames, wherein determination of the optimal TI frame occurs in a single pass.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein:

FIG. 6 illustrates various tables related to the optimal TI frame estimator model or network 248 in FIG. 5, in accordance with aspects of the present disclosure;

DETAILED DESCRIPTION

Figure 1:
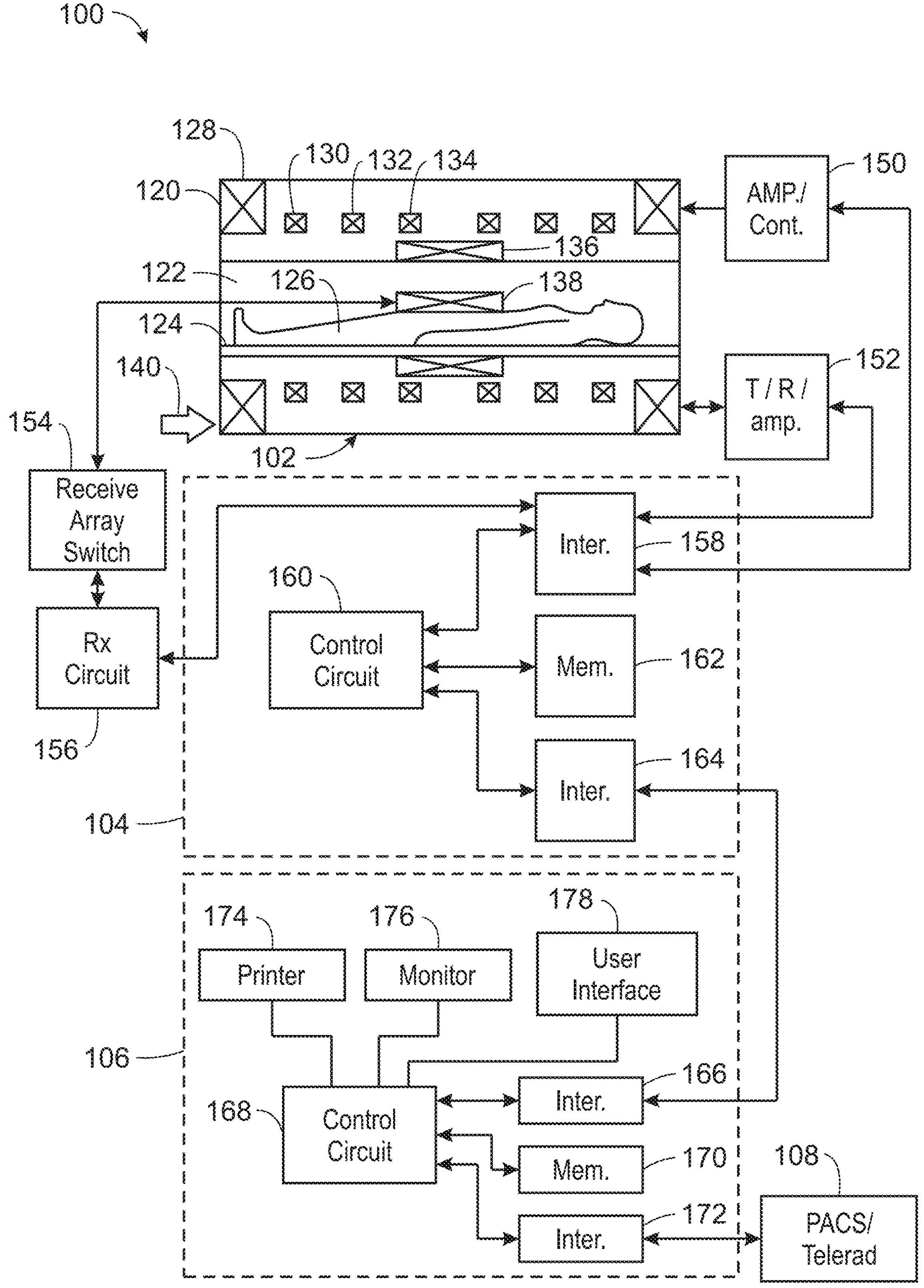
FIG. 1 illustrates an embodiment of a magnetic resonance imaging (MRI) system suitable for use with the disclosed technique, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion are provided in the context of medical imaging, it should be appreciated that the disclosed techniques are not limited to such medical contexts. Indeed, the provision of examples and explanations in such a medical context is only to facilitate explanation by providing instances of real-world implementations and applications. However, the disclosed techniques may also be utilized in other contexts, such as image reconstruction for non-destructive inspection of manufactured parts or goods (i.e., quality control or quality review applications), and/or the non-invasive inspection of packages, boxes, luggage, and so forth (i.e., security or screening applications). In general, the disclosed techniques may be useful in any imaging or screening context or image processing or photography field where a set or type of acquired data undergoes a reconstruction process to generate an image or volume.

Deep-learning (DL) approaches discussed herein may be based on artificial neural networks, and may therefore encompass one or more of deep neural networks, fully connected networks, convolutional neural networks (CNNs), unrolled neural networks, perceptrons, encoders-decoders, recurrent networks, wavelet filter banks, u-nets, general adversarial networks (GANs), dense neural networks, or other neural network architectures. The neural networks may include shortcuts, activations, batch-normalization layers, and/or other features. These techniques are referred to herein as DL techniques, though this terminology may also be used specifically in reference to the use of deep neural networks, which is a neural network having a plurality of layers.

As discussed herein, DL techniques (which may also be known as deep machine learning, hierarchical learning, or deep structured learning) are a branch of machine learning techniques that employ mathematical representations of data and artificial neural networks for learning and processing such representations. By way of example, DL approaches may be characterized by their use of one or more algorithms to extract or model high level abstractions of a type of data-of-interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data. In general, the processing from one representation space to the next-level representation space can be considered as one 'stage' of the process. Each stage of the process can be performed by separate neural networks or by different parts of one larger neural network.

In the following disclosure, the techniques are discussed with regard to MRI. The techniques may also be utilized for dynamic data characterization in other imaging modalities.

The present disclosure provides systems and methods for determining an optimal inversion time. In particular, disclosed systems and methods combining localization of a region (e.g., temporal span) containing an optimal TI frame and then determining an exact TI value in the localized region. Specifically, only a rough cardiac region localization is needed followed by utilizing the temporal information from an entire image (which provides resilience to local changes) and then predicting the optimal TI. The determination of the optimal inversion time occurs in a single pass or one-shot irrespective of the subjectivity of a TI-scout protocol and/or patient condition variations. In particular, the disclosed systems and methods quickly localize a transition area (including phase changes in the cardiac region including blood-pool nulling, remote myocardium, and initial recovery) based on a frame-wise feature distance metric. The disclosed systems and methods without organ segmentation or pre-processing, thus, making the solution very lightweight. The disclosed systems and methods utilizing advanced intelligent blocks like frame attention and spatial attention to accurately predict the inversion time while supporting multiple views (including 4-chamber views, 3-chamber views, 2-chamber views, axial views, long axial views (4 chamber), and short-axis views).

With the preceding in mind, FIG. 1 a magnetic resonance imaging (MRI) system 100 is illustrated schematically as including a scanner 102, scanner control circuitry 104, and system control circuitry 106. According to the embodiments described herein, the MRI system 100 is generally configured to perform MR imaging.

System 100 additionally includes remote access and storage systems or devices such as picture archiving and communication systems (PACS) 108, or other devices such as teleradiology equipment so that data acquired by the system 100 may be accessed on- or off-site. In this way, MR data may be acquired, followed by on- or off-site processing and evaluation. While the MRI system 100 may include any suitable scanner or detector, in the illustrated embodiment, the system 100 includes a full body scanner 102 having a housing 120 through which a bore 122 is formed. A table 124 is moveable into the bore 122 to permit a patient 126 (e.g., subject) to be positioned therein for imaging selected anatomy within the patient.

Scanner 102 includes a series of associated coils for producing controlled magnetic fields for exciting the gyromagnetic material within the anatomy of the patient being imaged. Specifically, a primary magnet coil 128 is provided for generating a primary magnetic field, $B_0$, which is generally aligned with the bore 122. A series of gradient coils 130, 132, and 134 permit controlled magnetic gradient fields to be generated for positional encoding of certain gyromagnetic nuclei within the patient 126 during examination sequences. A radio frequency (RF) coil 136 (e.g., RF transmit coil) is configured to generate radio frequency pulses for exciting the certain gyromagnetic nuclei within the patient. In addition to the coils that may be local to the scanner 102, the system 100 also includes a set of receiving coils or RF receiving coils 138 (e.g., an array of coils) configured for placement proximal (e.g., against) to the patient 126. As an example, the receiving coils 138 can include cervical/thoracic/lumbar (CTL) coils, head coils, single-sided spine coils, and so forth. Generally, the receiving coils 138 are placed close to or on top of the patient 126 so as to receive the weak RF signals (weak relative to the transmitted pulses generated by the scanner coils) that are generated by certain gyromagnetic nuclei within the patient 126 as they return to their relaxed state.

The various coils of system 100 are controlled by external circuitry to generate the desired field and pulses, and to read emissions from the gyromagnetic material in a controlled manner. In the illustrated embodiment, a main power supply 140 provides power to the primary field coil 128 to generate the primary magnetic field, Bo. A power input (e.g., power from a utility or grid), a power distribution unit (PDU), a power supply (PS), and a driver circuit 150 may together provide power to pulse the gradient field coils 130, 132, and 134. The driver circuit 150 may include amplification and control circuitry for supplying current to the coils as defined by digitized pulse sequences output by the scanner control circuitry 104.

Another control circuit 152 is provided for regulating operation of the RF coil 136. Circuit 152 includes a switching device for alternating between the active and inactive modes of operation, wherein the RF coil 136 transmits and does not transmit signals, respectively. Circuit 152 also includes amplification circuitry configured to generate the RF pulses. Similarly, the receiving coils 138 are connected to switch 154, which is capable of switching the receiving coils 138 between receiving and non-receiving modes. Thus, the receiving coils 138 resonate with the RF signals produced by relaxing gyromagnetic nuclei from within the patient 126 while in the receiving mode, and they do not resonate with RF energy from the transmitting coils (i.e., coil 136) so as to prevent undesirable operation while in the non-receiving mode. Additionally, a receiving circuit 156 is configured to receive the data detected by the receiving coils 138 and may include one or more multiplexing and/or amplification circuits.

It should be noted that while the scanner 102 and the control/amplification circuitry described above are illustrated as being coupled by a single line, many such lines may be present in an actual instantiation. For example, separate lines may be used for control, data communication, power transmission, and so on. Further, suitable hardware may be disposed along each type of line for the proper handling of the data and current/voltage. Indeed, various filters, digitizers, and processors may be disposed between the scanner and either or both of the scanner and system control circuitry 104, 106.

As illustrated, scanner control circuitry 104 includes an interface circuit 158, which outputs signals for driving the gradient field coils and the RF coil and for receiving the data representative of the magnetic resonance signals produced in examination sequences. The interface circuit 158 is coupled to a control and analysis circuit 160. The control and analysis circuit 160 executes the commands for driving the circuit 150 and circuit 152 based on defined protocols selected via system control circuit 106.

Control and analysis circuit 160 also serves to receive the magnetic resonance signals and performs subsequent processing before transmitting the data to system control circuit 106. Scanner control circuit 104 also includes one or more memory circuits 162, which store configuration parameters, pulse sequence descriptions, examination results, and so forth, during operation.

Interface circuit 164 is coupled to the control and analysis circuit 160 for exchanging data between scanner control circuitry 104 and system control circuitry 106. In certain embodiments, the control and analysis circuit 160, while illustrated as a single unit, may include one or more hardware devices. The system control circuit 106 includes an interface circuit 166, which receives data from the scanner control circuitry 104 and transmits data and commands back to the scanner control circuitry 104. The control and analysis circuit 168 may include a CPU in a multi-purpose or application specific computer or workstation. Control and analysis circuit 168 is coupled to a memory circuit 170 to store programming code for operation of the MRI system 100 and to store the processed image data for later reconstruction, display and transmission. The programming code may execute one or more algorithms that, when executed by a processor, are configured to perform reconstruction of acquired data as described below. In certain embodiments, the memory circuit 170 may store one or more neural networks. For example, the neural networks may include a first trained neural network (e.g., region of interest (ROI) detection model or network) for localizing a cardiac region in the TI-scout MIP image to generate a region of interest (ROI) segmentation mask for the cardiac region. The neutral networks may also include a second trained neural network (e.g., optimal TI frame estimator model or network) for determining or estimating an optimal TI frame. The neural networks form a deep learning-based neural framework. In certain embodiments, the techniques disclosed herein may occur on a separate computing device having processing circuitry and memory circuitry.

A processing component (e.g., a microprocessor or processing circuitry) and a memory of the magnetic resonance imaging system 100, such as may be present in scanner control circuitry 104 and/or system control circuitry 106, may be used to execute stored software code, instructions, or routines for acquiring and processing the MR data. The term "code" or "software code" used herein refers to any instructions or set of instructions that control the magnetic resonance imaging system 100. The code or software code may exist in a computer-executable form, such as machine code, which is the set of instructions and data directly executed by the processing component of the scanner control circuitry 104 and/or system control circuitry 106, human-understandable form, such as source code, which may be compiled in order to be executed by the processing component of the scanner control circuitry 104 and/or system control circuitry 106, or an intermediate form, such as object code, which is produced by a compiler. In some embodiments, the magnetic resonance imaging system 100 may include a plurality of controllers.

As an example, the memory may store processor-executable software code or instructions (e.g., firmware or software), which are tangibly stored on a non-transitory computer readable medium. Additionally or alternatively, the memory may store data. As an example, the memory may include a volatile memory, such as random-access memory (RAM), and/or a nonvolatile memory, such as read-only memory (ROM), flash memory, a hard drive, or any other suitable optical, magnetic, or solid-state storage medium, or a combination thereof. Furthermore, processing component may include multiple microprocessors, one or more "general-purpose" microprocessors, one or more special-purpose microprocessors, and/or one or more application specific integrated circuits (ASICS), or some combination thereof. For example, the processing component may include one or more reduced instruction set (RISC) or complex instruction set (CISC) processors. The processing component may include multiple processors, and/or the memory may include multiple memory devices.

In certain embodiments (e.g., for determining an optimal inversion time (TI) in a one-shot or a single pass), the processing component is configured to obtain a series of magnetic resonance (MR) scout temporal frames of a subject from MR scout imaging data acquired with an MR scanner utilizing a TI-scout sequence. In certain embodiments, the series of MR scout temporal frames include 4-chamber views, 3-chamber views, 2-chamber views, axial views, long axial views, or short-axis views. The processing component is configured to obtain a TI-scout maximum intensity projection (MIP) image from the MR scout imaging data. The processing component is configured to utilize a first trained neural network to localize a cardiac region in the TI-scout MIP image to generate a region of interest (ROI) segmentation mask for the cardiac region. The processing component is configured to utilize the ROI segmentation mask on the TI-scout MIP image and the series of MR scout temporal frames to generate a ROI cropped TI-scout MIP image and ROI cropped MR scout temporal frames, respectively. The processing component is configured to generate a distance score plot by computing a distance between each ROI cropped MR scout temporal frame and the ROI cropped TI-scout MIP image. The processing component is configured to automatically analyze the distance score plot to approximate a span of the MR scout temporal frames for optimal TI frame estimation, wherein the span of the MR scout temporal frames encompasses a transition region including phase changes in the cardiac region including blood-pool nulling, remote myocardium nulling, and initial recovery. The processing component is configured to utilize a second trained neural network to determine an optimal TI frame from the span of the MR scout temporal frames, wherein determination of the optimal TI frame occurs in a single pass.

In certain embodiments, the processing component may be configured, prior to generating the distance score plot, to normalize the ROI cropped TI-scout MIP image and the ROI cropped MR scout temporal frames. In certain embodiments, the processing component may be configured, when automatically analyzing the distance score plot to approximate the span of the MR scout temporal frames for optimal TI frame estimation, to determine a point on the distance score plot having a maximum distance, wherein the point represents the transition region and to select a number of temporally consecutive frames from the series of MR scout temporal frames that both flank and include the transition region as the span of the MR scout temporal frames.

In certain embodiments, the processing component may be configured to train a neural network to generate the second trained neural network utilizing the ROI cropped MR scout temporal frames with a temporal window size large enough to provide accurate estimation of the optimal TI frame for the blood-pool and/or myocardium. In certain embodiments, the span of the MR scout temporal frames is within the temporal window size.

In certain embodiments, the processing component may be configured, when utilizing the second trained neural network to determine TI optimal TI frame, to input into the second trained neural network the span of the MR scout temporal frames and the ROI segmentation mask and to output from the second trained neural network an optimal TI frame from the span of MR scout temporal frames. In certain embodiments, the processing component may be configured to utilize the second trained neural network to determine the optimal TI frame comprises predicting a score between 0 and 1 for each MR scout temporal frame within the span, wherein the score for the optimal TI frame is close to or at 1. In certain embodiments, the processing component may be configured to output a user-perceptible indication when none of the MR scout temporal frames within the span have a respective score high enough to be considered the optimal TI frame. In certain embodiments, the processing component may be configured to output a user-perceptible indication of an optimal TI based on the optimal TI frame and a pulse sequence diagram of the TI-scout sequence.

An additional interface circuit 172 may be provided for exchanging image data, configuration parameters, and so forth with external system components such as remote access and storage devices 108. Finally, the system control and analysis circuit 168 may be communicatively coupled to various peripheral devices for facilitating operator interface and for producing hard copies of the reconstructed images. In the illustrated embodiment, these peripherals include a printer 174, a monitor 176, and user interface 178 including devices such as a keyboard, a mouse, a touchscreen (e.g., integrated with the monitor 176), and so forth.

Figure 2:
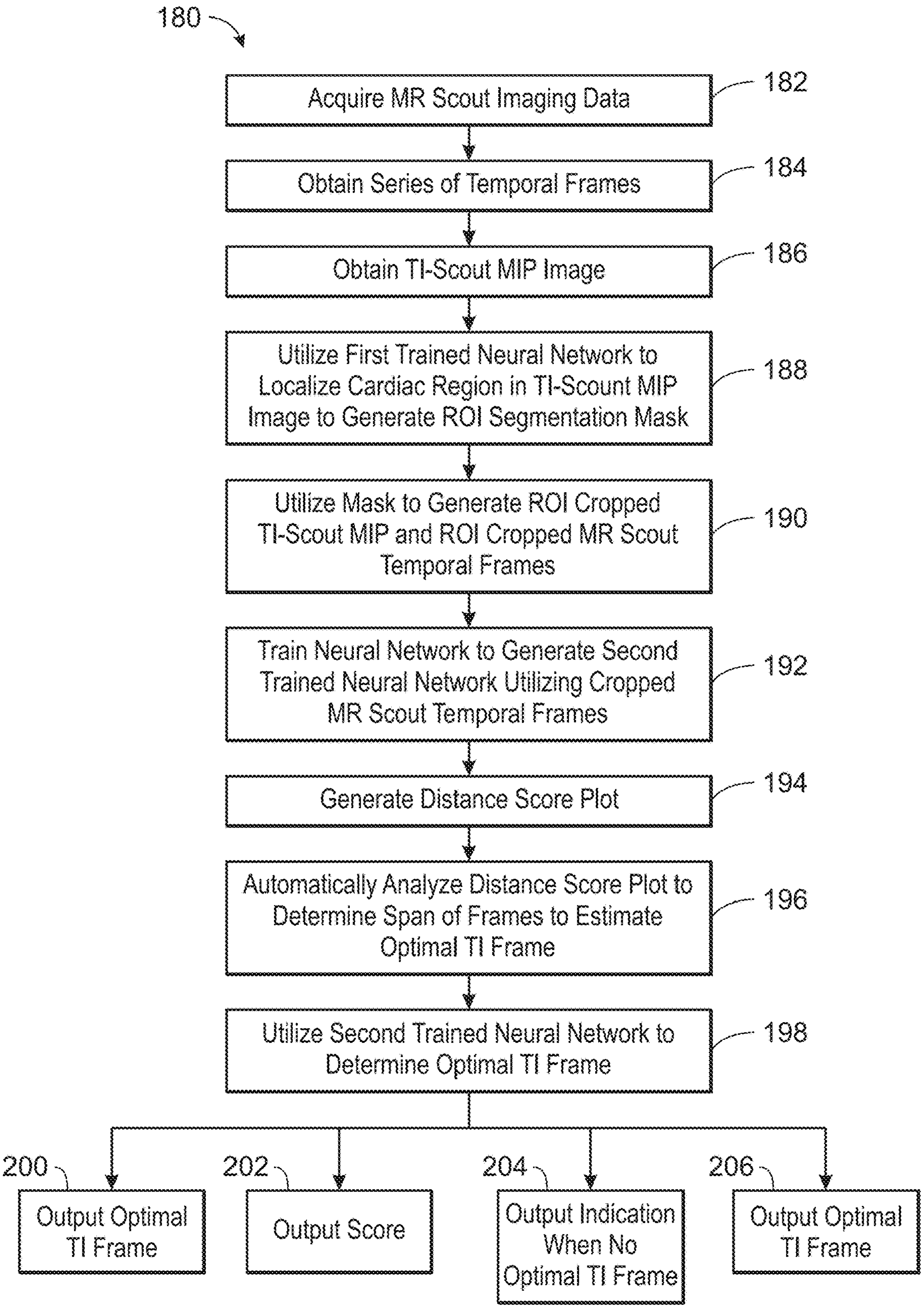
FIG. 2 illustrates a flow diagram of a method for determining an optimal inversion time (TI), in accordance with aspects of the present disclosure.

FIG. 2 illustrates a flow diagram of a method 180 for determining an optimal inversion time (TI). One or more steps of the method 180 may be performed by processing circuitry of the magnetic resonance imaging system 100 in FIG. 1 or a remote computing device. One or more of the steps of the method 180 may be performed simultaneously and/or in a different order from that depicted in FIG. 2. The method 180 supports multiple views (i.e., 4-chamber views, 3-chamber views, 2-chamber views, axial views, long axial views (4 chamber), and short-axis views).

The method 180 includes acquiring MR scout imaging data (e.g., three-dimensional (3D) imaging data) of a subject (e.g., of a chest region of a subject) with an MR scanner utilizing a TI-scout sequence (block 182). The method 180 also includes obtaining a series of magnetic resonance (MR) scout temporal frames of a subject from the MR scout imaging data acquired with the MR scanner utilizing the TI-scout sequence (block 184). The method 180 further includes obtaining a TI-scout maximum intensity projection (MIP) image from the MR scout imaging data (block 186). The method 180 even further includes utilizing a first trained neural network (e.g., region of interest (ROI) detection model or network) to localize a cardiac region in the TI-scout MIP image to generate a region of interest (ROI) segmentation mask for the cardiac region (block 188). In certain embodiments, the first trained neural network is configured to utilize an object detection approach. In certain embodiments, the first trained neural network is configured to utilize a semantic segmentation approach. The method 180 even further includes utilizing the ROI segmentation mask on the TI-scout MIP image and the series of MR scout temporal frames to generate a ROI cropped TI-scout MIP image and ROI cropped MR scout temporal frames, respectively (block 190).

The method 180 includes training a neural network to generate a second trained neural network (e.g., optimal TI frame estimator model or network) utilizing the ROI segmentation mask and a subset of the MR scout temporal frames with a temporal window size large enough to provide accurate estimation of an optimal TI frame in a transition region (e.g., during a localized transition) that includes phase changes in a myocardium (e.g., blood-pool nulling, remote myocardium nulling, and initial recovery) during the TI-scout sequence (block 192). The second trained neural network is configured to determine or estimate an optimal TI frame. As described in greater detail below, in certain embodiments, the second trained neural network is dual attention (Datt) three-dimensional (3D) CNN. The method 180 still further includes generating a distance score plot by computing a distance between each ROI cropped MR scout temporal frame and the ROI cropped TI-scout MIP image (block 194). In certain embodiments, prior to generating the distance score plot, the ROI cropped TI-scout MIP image and the ROI cropped MR scout temporal frames are normalized. The method 180 further includes automatically analyzing the distance score plot to approximate a span of the MR scout temporal frames for optimal TI frame estimation, wherein the span of the MR scout temporal frames encompasses a transition region including phase changes in the cardiac region including blood-pool nulling, remote myocardium nulling, and initial recovery (block 196). The span of the MR scout temporal frames is within the temporal window size that is expected for the second trained neural network.

The method 180 further includes utilizing the second trained neural network to determine the optimal TI frame from the span of the MR scout temporal frames, wherein determination of the optimal TI frame occurs in a single pass (or one-shot) (block 198). In certain embodiments, utilizing the second trained neural network to determine the optimal TI frame includes inputting into the second trained neural network the span of the MR scout temporal frames. In certain embodiments, the method 180 includes outputting from the second trained neural network the optimal TI frame from the span (e.g., for display) (block 200). In certain embodiments, utilizing the second trained neural network to determine the optimal TI frame includes predicting a score (prediction probability score) between 0 and 1 for each MR scout temporal frame within the span, wherein the score for the TI frame is close to or at 1. In certain embodiments, the scores are compared to a threshold (e.g., 0.5 or another set threshold) and only scores at or above the threshold can potentially be considered the optimal TI. In certain embodiments, the method 180 includes outputting the score for the optimal TI frame (and in certain embodiments other frames) (block 202). In certain embodiments, the method 180 includes outputting a user-perceptible indication (and in certain embodiments, feedback to why or how to improve analysis) when none of the scout temporal frames within the span have a respective score high enough (e.g., about the threshold) to be considered the optimal TI frame (e.g., due to disease) (block 204). In certain embodiments, the method 180 includes outputting user-perceptible indication of an optimal TI based on the optimal TI frame and pulse sequence diagram of the TI-scout sequence (block 206).

Figure 3:
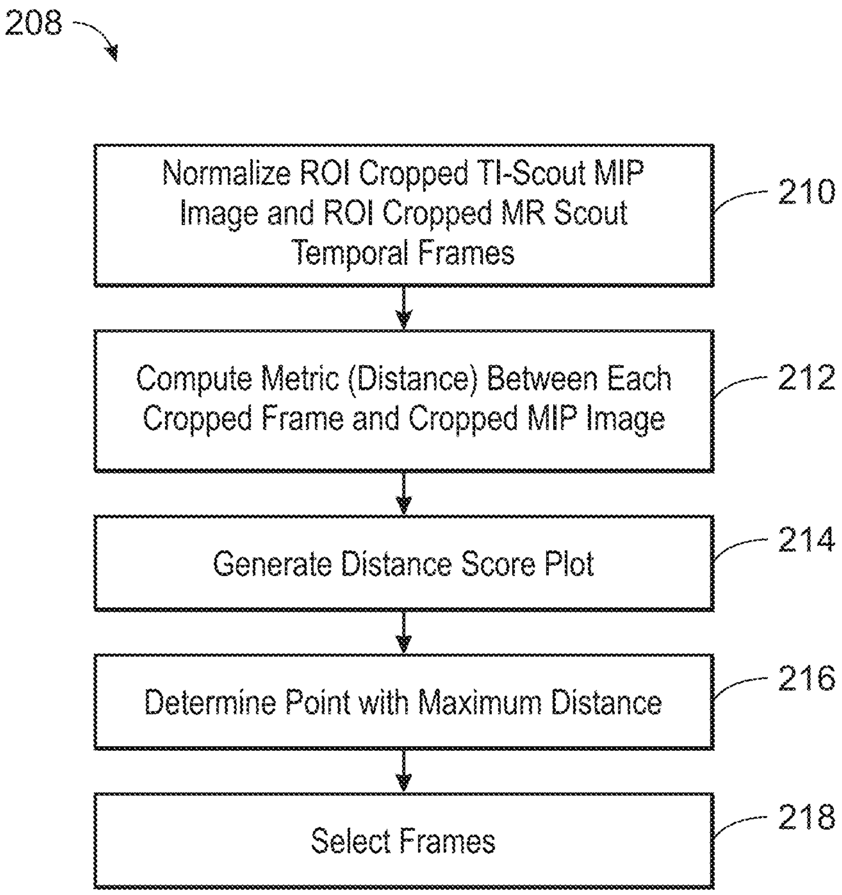
FIG. 3 illustrates a flow diagram of method for determining a local transition region, in accordance with aspects of the present disclosure.

FIG. 3 illustrates a flow diagram of method 208 for determining a local transition region. One or more steps of the method 208 may be performed by processing circuitry of the magnetic resonance imaging system 100 in FIG. 1 or a remote computing device.

The method 208 includes normalizing the ROI cropped TI-scout MIP image and the ROI cropped MR scout temporal frames (obtained as described in the method 180 in FIG. 2) (block 210). Each data frame (i.e., ROI cropped MR scout temporal frame) is normalized between 0 to 1. The method 208 also includes computing the metric (Jensen-Shannon distance) (e.g., distance) between each normalized ROI cropped MR scout temporal frame and the normalized ROI cropped TI-scout MIP image (block 212). The Jenson-Shannon measures the dissimilarity between the two probability distributions (i.e., of a respective normalized ROI cropped MR scout temporal frame and the normalized ROI cropped TI-scout MIP image. The equation utilized for calculating the metric (distance, $d_{JS}$) is as follows:

$$d_{JS} = \frac{1}{2}\left[\sum_{i=1}^{d} P_i \ln\left(\frac{2P_i}{P_i + Q_i}\right) + \sum_{i=1}^{d} Q_i \ln\left(\frac{2Q_i}{P_i + Q_i}\right)\right] \quad (1)$$

where P represents the probability distribution for the normalized ROI cropped TI-scout MIP image and Q represents the probability distribution of the respective normalized ROI cropped MR scout temporal frame.

The method 208 further includes generating a distance score plot based on the computed metrics (block 214). The method 208 even further includes determining a point (and corresponding frame) which has maximum distance (from among all computed distances) within the distance score plot (block 216). The point is the transition region. The method 208 still further includes selecting the frames (i.e., the span of frames) for one-shot prediction as input into the second trained neural network (as described above in the method 180 in FIG. 2) (block 218).

Figure 4:
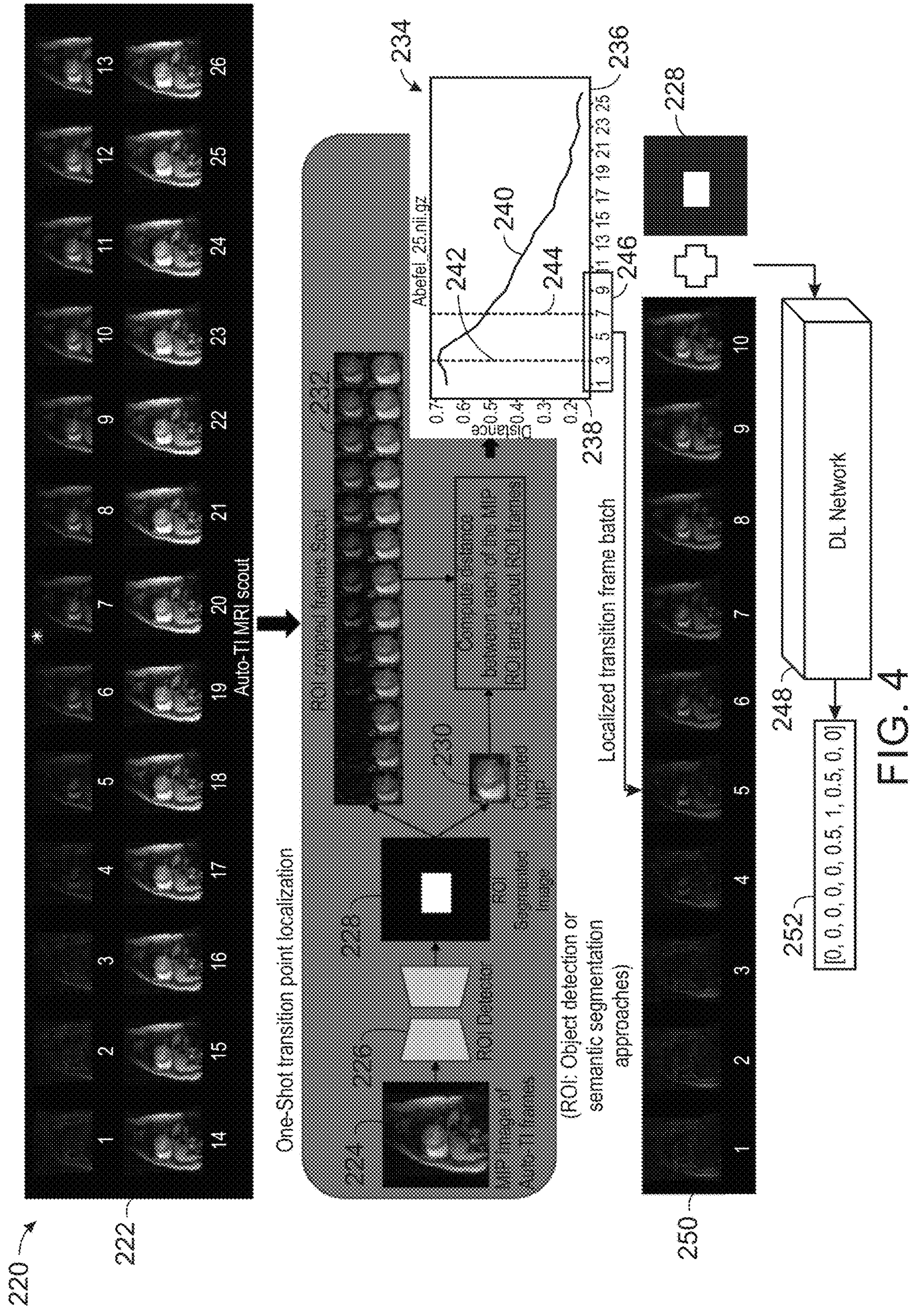
FIG. 4 illustrates a schematic diagram of process for determining an optimal inversion time (TI), in accordance with aspects of the present disclosure.

FIG. 4 illustrates a schematic diagram of process 220 for determining an optimal inversion time (TI). The process 220 includes obtaining a series of magnetic resonance (MR) scout temporal frames 222 of a subject from the MR scout imaging data acquired with the MR scanner utilizing the TI-scout sequence. The process 220 further includes obtaining a TI-scout maximum intensity projection (MIP) image 224 from the MR scout imaging data. The process 220 includes utilizing the series of MR scout temporal frames 222 and the TI-scout MIP image 224 in performing one-shot transition point localization. In particular, the process 220 includes utilizing a first trained neural network 226 (e.g., region of interest (ROI) detection model or network) to localize a cardiac region in the TI-scout MIP image 224 to generate a region of interest (ROI) segmentation mask 228 for the cardiac region. In certain embodiments, the first trained neural network 226 is configured to utilize an object detection approach. In certain embodiments, the first trained neural network 226 is configured to utilize a semantic segmentation approach. The process 220 includes utilizing the ROI segmentation mask 228 on the TI-scout MIP image 224 and the series of MR scout temporal frames 222 to generate a ROI cropped TI-scout MIP image 230 and ROI cropped MR scout temporal frames 232, respectively.

The process 220 still further includes generating a distance score plot 234 by computing a distance between each ROI cropped MR scout temporal frame 232 and the ROI cropped TI-scout MIP image 230 as described above in the method 208 in FIG. 3. As depicted, the distance score plot 234 includes an x-axis 236 representing a frame number of the ROI cropped MR scout temporal frames 232 and a y-axis 238 representing the calculated distance metric (e.g., Jensen-Shannon distance). Plot 240 represents the distance metric values for each of the frames 232. Dashed line 242 represents the determined transition region (i.e., maximum distance). Dashed line 242 represents the optimal TI point. In certain embodiments, prior to generating the distance score plot 234, the ROI cropped TI-scout MIP image 230 and the ROI cropped MR scout temporal frames 232 are normalized. The process 220 further includes automatically analyzing the distance score plot 234 to approximate a span (number of frames indicated by box 246 and referred to as the localized transition frame batch 250) of the MR scout temporal frames 222 (that correspond with the ROI cropped MR scout temporal frames 232) for optimal TI frame estimation, wherein the span of the MR scout temporal frames 222 encompasses a transition region including phase changes in the cardiac region including blood-pool nulling, remote myocardium nulling, and initial recovery (block 196). The number of frames utilized for the localized transition bath is an arbitrary number (e.g., 10) that flanks the transition point 242.

The span of the MR scout temporal frames 222 (or localized transition frame batch 250) is within the temporal window size that is expected for the second trained neural network 248 (e.g., optimal TI frame estimator model or network). The second trained neural network 248 was trained utilizing the ROI cropped MR scout temporal frames 232 with a temporal window size large enough to provide accurate estimation of an optimal TI frame in a transition region (e.g., during a localized transition) that includes phase changes in a myocardium (e.g., blood-pool nulling, remote myocardium nulling, and initial recovery) during the TI-scout sequence. The second trained neural network 248 is configured to determine or estimate an optimal TI frame. In certain embodiments, the second trained neural network 248 is dual attention (Datt) three-dimensional (3D) CNN.

As depicted in FIG. 4, the process 220 includes inputting the span of the MR scout temporal frames 222 (or localized transition frame batch 250) and the ROI segmentation mask 228 into the second trained neural network 248. The process 220 includes utilizing the second trained neural network 248 to determine the optimal TI frame from the span of the MR scout temporal frames (or localized transition frame batch 250), wherein determination of the optimal TI frame occurs in a single pass (or single-shot). As depicted, a score (e.g., prediction probability score) between 0 and 1 is outputted for each MR scout temporal frame 222 of the localized transition frame batch 250 as indicated by reference numeral 252.

Figure 5:
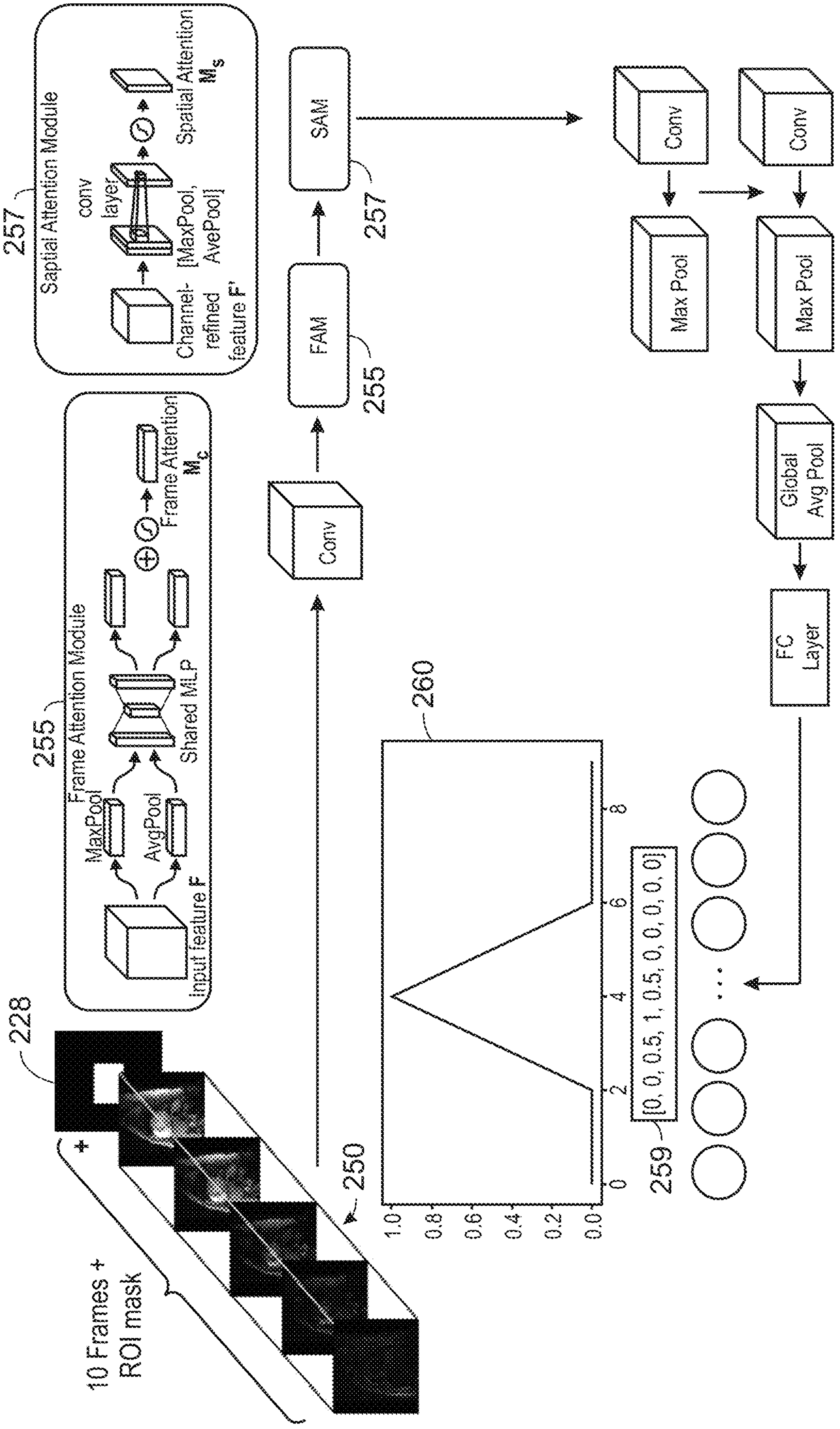
FIG. 5 illustrates a structure and a function of an optimal TI frame estimator model or network, in accordance with aspects of the present disclosure.

FIG. 5 illustrates a structure and a function of an optimal TI frame estimator model or network 248 (i.e., the second trained neural network). The structure of the network 248 may vary from that depicted in FIG. 5. As depicted, the optimal TI frame estimator model or network 248 is a dual attention 3D network. The optimal TI frame estimator model or network 248 includes both a frame attention module (FAM) 255 and a spatial attention module (SAM) 257. The cropping for training the optimal TI frame estimator model or network 248 is not done explicitly but implicitly by providing the ROI segmentation mask 228 as additional channel to make it resilient to any failures of the first trained neural network (i.e., ROI detection model or network 226 in FIG. 4). The FAM 255 (i.e., temporal attention module) enables better localization on the correct frame. The optimal TI frame estimator model or network 248 utilizes soft labels to incorporate any user bias in labeling. As depicted, localized transition frame batch 250 and the ROI segmentation mask 228 are inputted into the optimal TI frame estimator model or network 248. A temporal window of 10 was chosen based on the available data statistics. This temporal window is flexible while providing a good bound for a permissible temporal localization error. As depicted, the optimal TI frame estimator model or network 248 outputs a score (e.g., prediction probability score) between 0 and 1 for each MR scout temporal frame of the localized transition frame batch 250 as indicated by reference numeral 259 and a graph 260 plotting the scores of each frame of the localized transition frame batch 250. FIG. 6 depicts various tables 262, 264 related to the optimal TI frame estimator model or network 248 in FIG. 5. Table 262 depicts the number of test samples and training samples utilized for the optimal TI frame estimator model or network 248. Table 262 also depicts the frame ranges of the test samples and the training samples. Table 264 depicts the accuracy of the optimal TI frame estimator model or network 248 within +1 frame and the number of parameters of the optimal TI frame estimator model or network 248.

Figure 7:
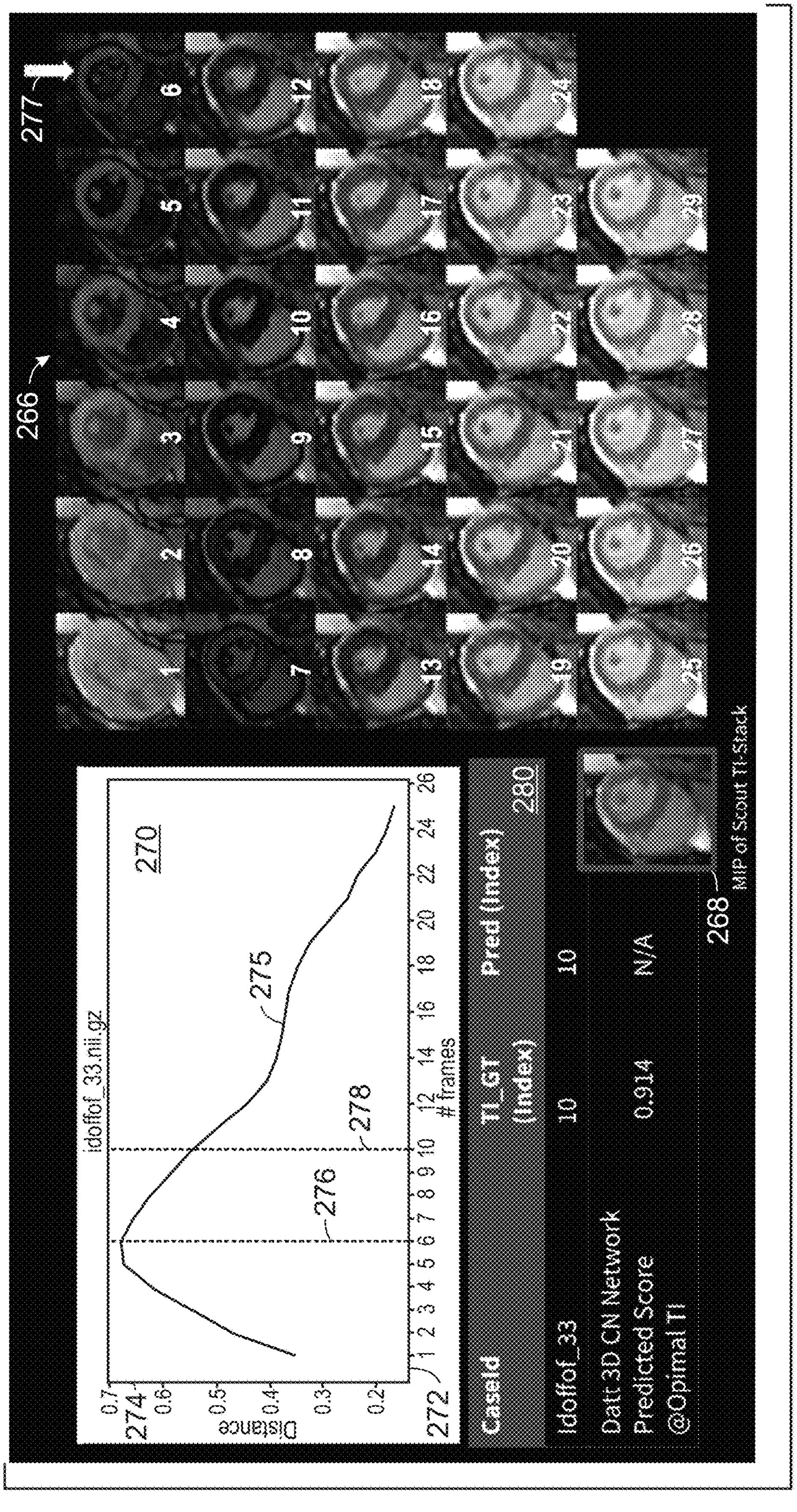
FIG. 7 illustrates a first example of the utilization of the optimal TI frame estimator model or network in FIG. 5, in accordance with aspects of the present disclosure.

FIG. 7 depicts a first example of the utilization of the optimal TI frame estimator model or network 248 in FIG. 5. The series of MR scout temporal frames 266 (e.g., short-axis views) are depicted on the right of FIG. 7. Image 268 represents the TI-scout MIP image. Graph 270 on the upper left of FIG. 7 is a distance score plot that includes an x-axis 272 representing a frame number of the ROI cropped MR scout temporal frames and a y-axis 274 representing the calculated distance metric (e.g., Jensen-Shannon distance). Plot 275 represents the distance metric values for each of the frames. Dashed line 276 represents the determined transition region (i.e., maximum distance). Arrow 277 depicts the frame with the localized transition point. Dashed line 278 represents the optimal TI point. Table 280 on the lower left of FIG. 7 compares the ground truth for the optimal TI frame to the optimal TI frame predicted by the optimal TI frame estimator model or network 248 in FIG. 5. As depicted, the predicted optimal TI frame is the same as the ground truth optimal TI frame. The table 280 also provides the predicted scored for the predicted optimal TI frame (which is near 1).

Figure 8:
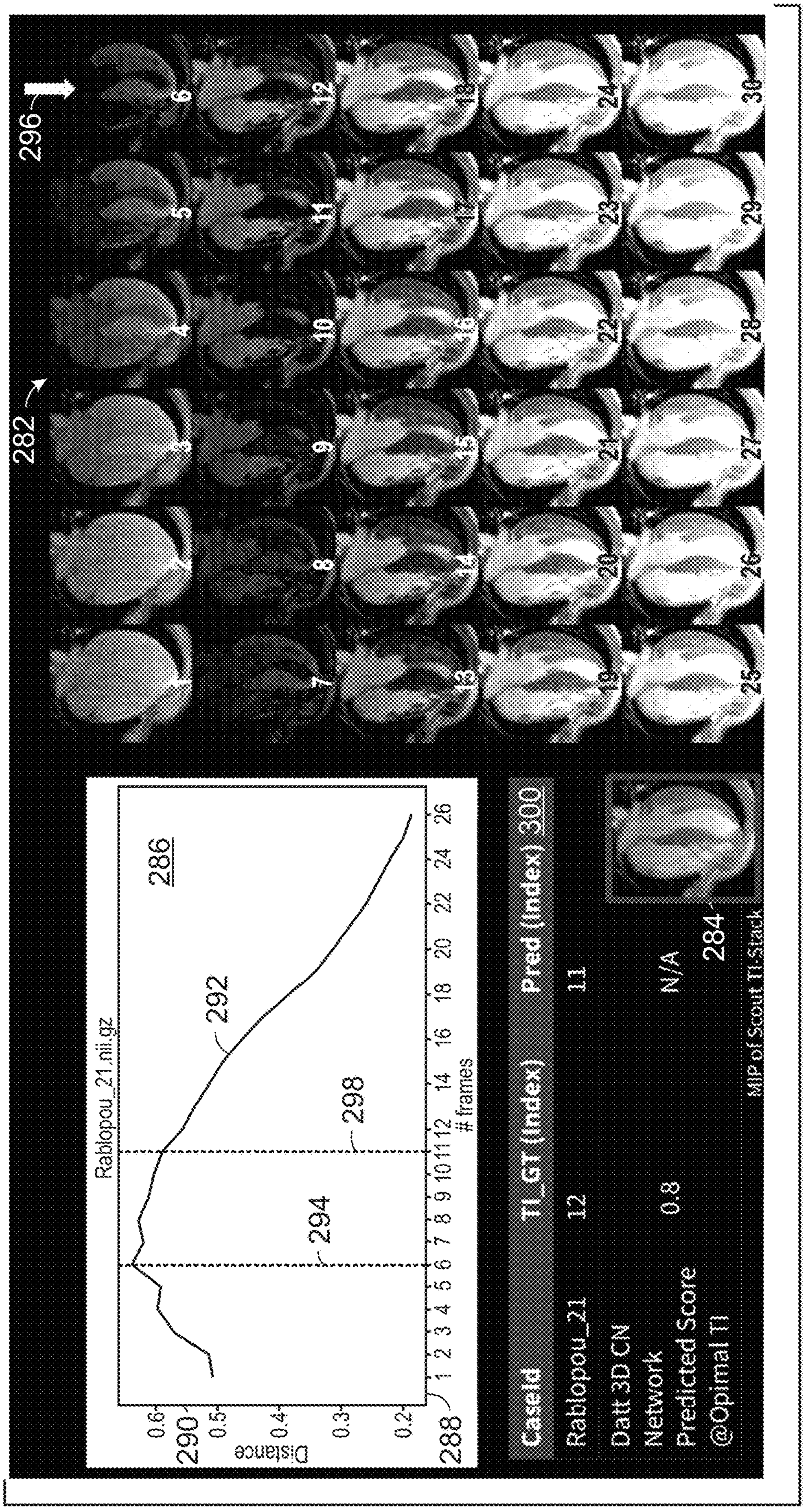
FIG. 8 illustrates a second example of the utilization of the optimal TI frame estimator model or network in FIG. 5, in accordance with aspects of the present disclosure.

FIG. 8 depicts a second example of the utilization of the optimal TI frame estimator model or network 248 in FIG. 5. The series of MR scout temporal frames 282 (e.g., long axis view) are depicted on the right of FIG. 8. Image 284 represents the TI-scout MIP image. Graph 286 on the upper left of FIG. 8 is a distance score plot that includes an x-axis 288 representing a frame number of the ROI cropped MR scout temporal frames and a y-axis 290 representing the calculated distance metric (e.g., Jensen-Shannon distance). Plot 292 represents the distance metric values for each of the frames. Dashed line 294 represents the determined transition region (i.e., maximum distance). Arrow 296 depicts the frame with the localized transition point. Dashed line 298 represents the optimal TI point. Table 300 on the lower left of FIG. 8 compares the ground truth for the optimal TI frame to the optimal TI frame predicted by the optimal TI frame estimator model or network 248 in FIG. 5. As depicted, the predicted optimal TI frame is within one frame of the ground truth optimal TI frame. The table 300 also provides the predicted scored for the predicted optimal TI frame (which is near 1).

Figure 9:
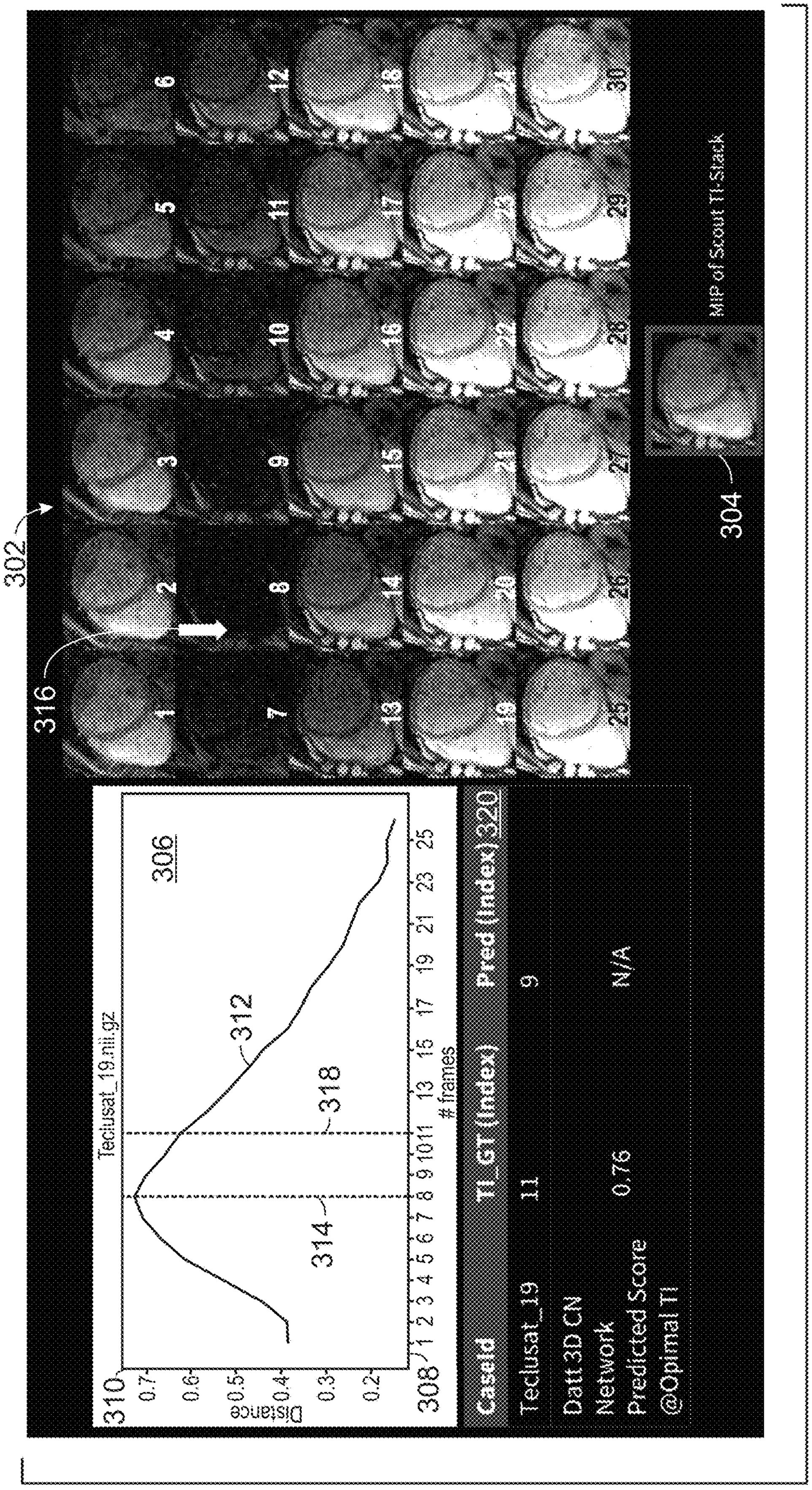
FIG. 9 illustrates a third example of the utilization of the optimal TI frame estimator model or network in FIG. 5, in accordance with aspects of the present disclosure.

FIG. 9 depicts a third example of the utilization of the optimal TI frame estimator model or network 248 in FIG. 5. The series of MR scout temporal frames 302 (e.g., short-axis view) are depicted on the right of FIG. 9. Image 304 represents the TI-scout MIP image. Graph 306 on the upper left of FIG. 9 is a distance score plot that includes an x-axis 308 representing a frame number of the ROI cropped MR scout temporal frames and a y-axis 310 representing the calculated distance metric (e.g., Jensen-Shannon distance). Plot 312 represents the distance metric values for each of the frames. Dashed line 314 represents the determined transition region (i.e., maximum distance). Arrow 316 depicts the frame with the localized transition point. Dashed line 318 represents the optimal TI point. Table 320 on the lower left of FIG. 9 compares the ground truth for the optimal TI frame to the optimal TI frame predicted by the optimal TI frame estimator model or network 248 in FIG. 5. As depicted, the predicted optimal TI frame is within two frames of the ground truth optimal TI frame. The table 320 also provides the predicted scored for the predicted optimal TI frame (which is near 1).

Figure 10:
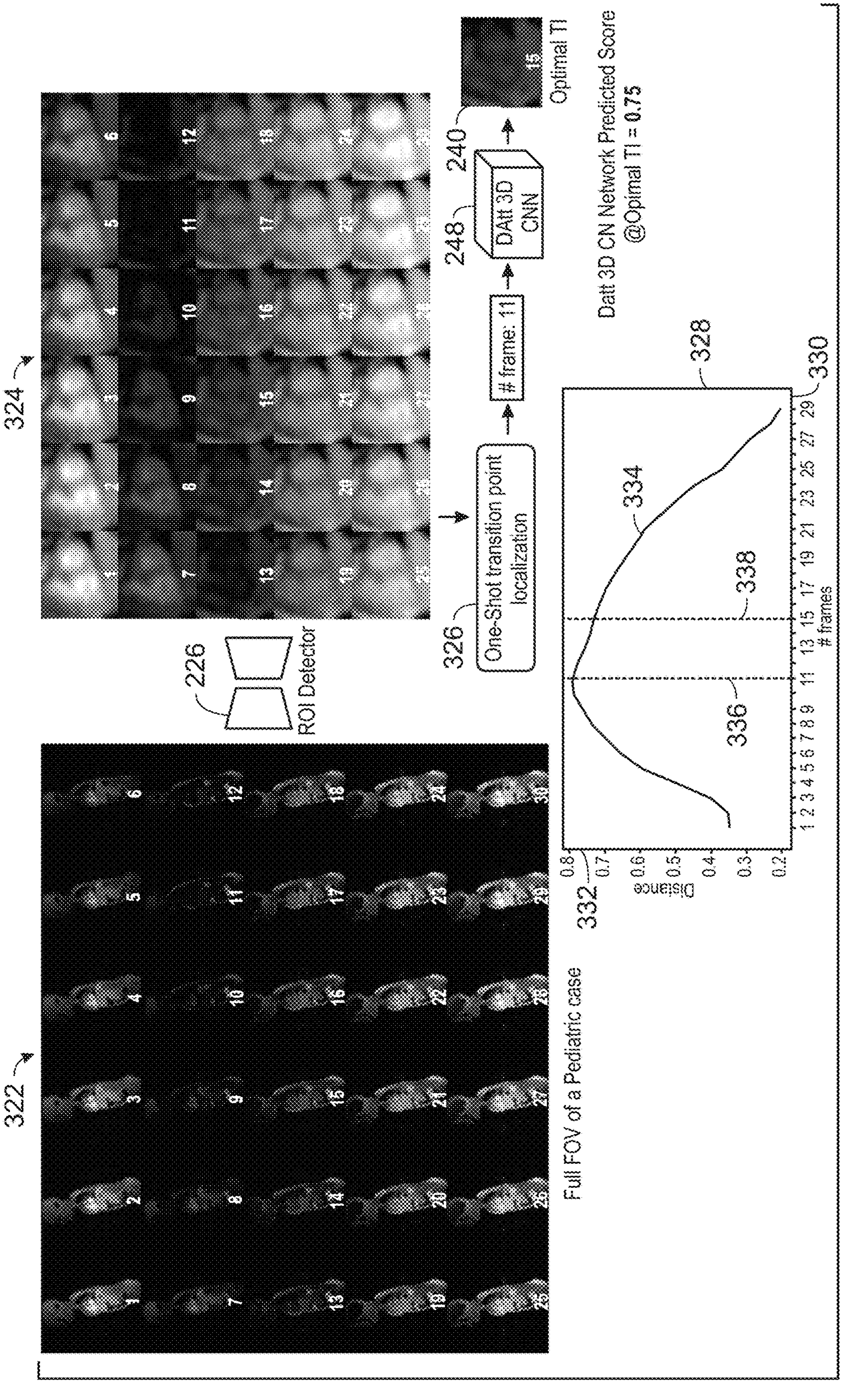
FIG. 10 illustrates an example of utilization of the optimal TI frame estimator model or network in FIG. 5 on a pediatric subject being scanned, in accordance with aspects of the present disclosure.

FIG. 10 illustrates an example of utilization of the optimal TI frame estimator model or network 248 in FIG. 5 on a pediatric subject being scanned. The left side of FIG. 10 depicts MR scout temporal frames 322 acquired of the pediatric subject. The first trained neural network 226 is utilized as described in the method 180 in FIG. 2 to generate the ROI cropped MR scout temporal frames 324 on the right side of FIG. 2. From one-shot transition point localization 326 (as described in the method 180 in FIG. 2 and the method 208 in FIG. 3), a distance score plot (i.e., graph 328). Graph 328 includes an x-axis 330 representing a frame number of the ROI cropped MR scout temporal frames and a y-axis 332 representing the calculated distance metric (e.g., Jensen-Shannon distance). Plot 334 represents the distance metric values for each of the frames. Dashed line 336 represents the determined transition region (i.e., maximum distance). Dashed line 338 represents the optimal TI point. As depicted, frame 11 represents the transition point. The optimal TI frame estimator model or network 248 outputs the optimal TI frame 340 (i.e., frame 15). FIG. 10 depicts how cardiac region localization brings in standardization irrespective of cardiac region being a frame of the image matrix size and results in a robust TI estimation.

Figure 11:
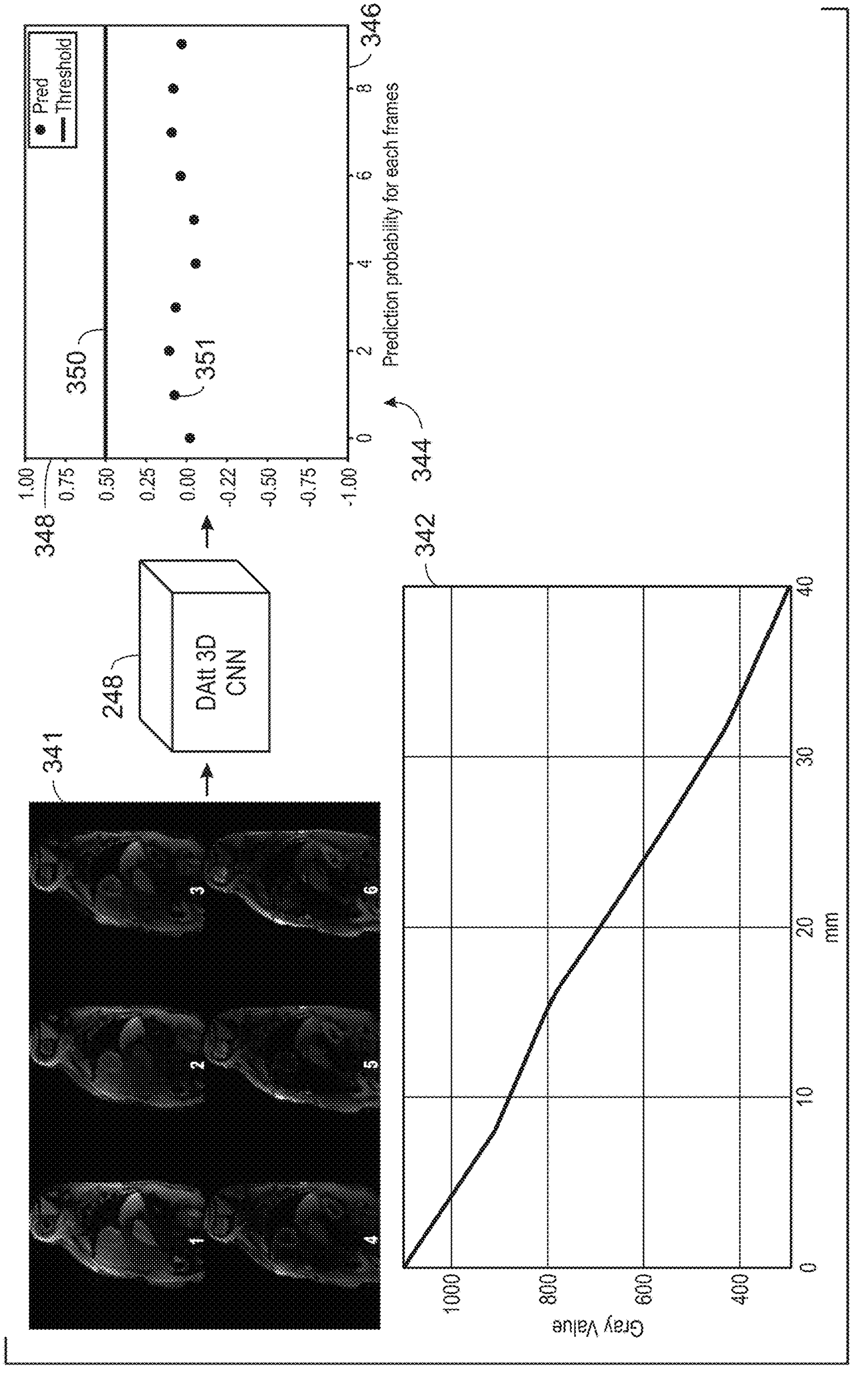
FIG. 11 illustrates an example of the utilization of the optimal TI frame estimator model or network in FIG. 5 (e.g., where optimal TI was not found and feedback is provided), in accordance with aspects of the present disclosure.

FIG. 11 illustrates an example of the utilization of the optimal TI frame estimator model or network 248 in FIG. 5 (e.g., where optimal TI was not found). The left side of FIG. 11 depicts the ROI cropped MR scout temporal frames 341 that are inputted into the optimal TI frame estimator model or network 248. The MR scout imaging data (from which the ROI cropped MR scout temporal frames 341 were obtained) was acquired during a free-breathing TI-scout. The TI window was not set correctly and hence myocardium nulling did not happen. This is depicted in table 342 which shows the signal intensity for the ROI placed in the myocardium has no bounce point. FIG. 11 depicts a graph 344 outputted from the optimal TI frame estimator model or network 248. Graph

344 includes an x-axis 346 representing the frame numbers and a y-axis 348 representing the prediction probability score. Line 350 represents the set threshold (i.e., 0.5). Points 351 represent the predicted probability scores for the frames. Each frame has a prediction probability score below 0.5 in graph 344. This means the scout was a negative scout. In such a case, a user-perceptible indication is provided indicating the lack of any optimal TI frame. In addition, a reason way may be provided and a recommendation may be provided (e.g., adjust TI used).

Figure 12:
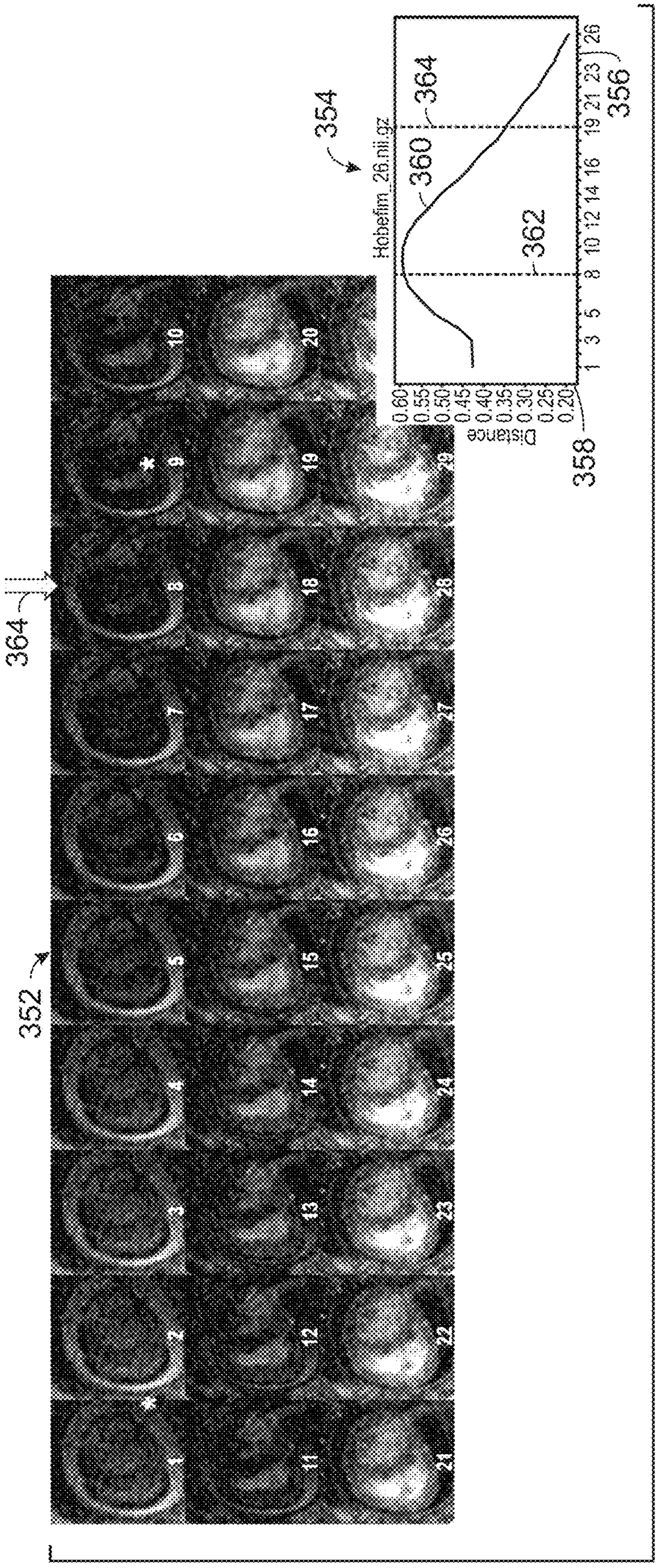
FIG. 12 illustrates an example of the utilization of the disclosed techniques for optimal TI frame estimation where optimal TI is difficult to determine, in accordance with aspects of the present disclosure.

FIG. 12 illustrates an example of the utilization of the disclosed techniques for optimal TI frame estimation where optimal TI is difficult to determine. The top of FIG. 12 depicts the ROI cropped MR scout temporal frames 352 that are utilized in the disclosed techniques. Graph 354 on the lower right of FIG. 12 is a distance score plot that includes an x-axis 356 representing a frame number of the ROI cropped MR scout temporal frames and a y-axis 358 representing the calculated distance metric (e.g., Jensen-Shannon distance). Plot 360 represents the distance metric values for each of the frames. Dashed line 362 represents the determined transition region (i.e., maximum distance). Arrow 364 depicts the frame with the localized transition point. Dashed line 366 represents the optimal TI point. In this case it was difficult to determine the optimal TI. However, the ground truth optimal TI provided from the site is also off. Even though an optimal TI mark could not be determined, the disclosed techniques were still useful in providing user guidance as to the most suitable region.

Technical effects of the disclosed subject matter include providing systems and methods for determining an optimal inversion time. Technical effects include determining the optimal inversion time in a faster and more accurate manner. Technical effects of the disclosed subject matter include enabling quickly localizing a region of interest in a temporal dimension without raster scanning an entire MR scout. Technical effects of the disclosed subject matter include bringing standardization into cardiac region localization so that performance is consistent irrespective of field of view, patient size, or view changes. Technical effects of the disclosed subject matter include providing a robot automatic TI solution which executes in a single shot (i.e., single pass) manner without having to resort to multiple passes and thereby reducing computing time. Technical effects of the disclosed subject matter include providing reliable and consistent myocardial delayed enhancement imaging despite variations in TI-scout protocol. Technical effects of the disclosed subject matter include utilizing deep learning-based automatic frame detection helps overcome any risks associated with alternate approaches consisting of segmentation of myocardium to determine optimal TI frame. Technical effects of the disclosed subject matter include, even in cases where optimal TI cannot be determined (e.g., due to disease), providing guidance to a user to the approximate temporal location for manual refinement without having to scroll through all frames. Technical effects of the disclosed subject matter include having no dependence on the number of frames or temporal scaling, thus, enabling adaptation to the subjectivity of the TI-scout protocols across sites. Technical effects of the disclosed subject matter include only needing a rough region of interest around the myocardium (via marking by a deep learning-based model) without the need for fine segmentation of cardiac anatomies. Technical effects of the disclosed subject matter include detecting if myocardium nullification has occurred in the scout sequence. Technical effects of the disclosed subject matter include providing a solution that supports multiple views (i.e., 4-chamber views, 3-chamber views, 2-chamber views, axial views, long axial views (4 chamber), and short-axis views).

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for determining an optimal inversion time (TI), comprising:

obtaining, via a processing system comprising one or more processors, a series of magnetic resonance (MR) scout temporal frames of a subject from MR scout imaging data acquired with an MR scanner utilizing a TI-scout sequence;

obtaining, via the processing system, a TI-scout maximum intensity projection (MIP) image from the MR scout imaging data;

utilizing, via the processing system, a first trained neural network to localize a cardiac region in the TI-scout MIP image to generate a region of interest (ROI) segmentation mask for the cardiac region;

utilizing, via the processing system, the ROI segmentation mask on the TI-scout MIP image and the series of MR scout temporal frames to generate a ROI cropped TI-scout MIP image and ROI cropped MR scout temporal frames, respectively;

generating, via the processing system, a distance score plot by computing a distance between each ROI cropped MR scout temporal frame and the ROI cropped TI-scout MIP image;

automatically analyzing, via the processing system, the distance score plot to approximate a span of the MR scout temporal frames for optimal TI frame estimation, wherein the span of the MR scout temporal frames encompasses a transition region comprising phase changes in the cardiac region including blood-pool nulling, remote myocardium nulling, and initial recovery; and utilizing, via the processing system, a second trained neural network to determine an optimal TI frame from the span of the MR scout temporal frames, wherein determination of the optimal TI frame occurs in a single pass.

2. The computer-implemented method of claim 1, further comprising, prior to generating the distance score plot, normalizing, via the processing system, the ROI cropped TI-scout MIP image and the ROI cropped MR scout temporal frames.

3. The computer-implemented method of claim 2, wherein automatically analyzing the distance score plot to approximate the span of the MR scout temporal frames for optimal TI frame estimation comprises:

determining a point on the distance score plot having a maximum distance, wherein the point represents the transition region; and selecting a number of temporally consecutive frames from the series of MR scout temporal frames that both flank and include the transition region as the span of the MR scout temporal frames.

4. The computer-implemented method of claim 1, further comprising training, via the processing system, a neural network to generate the second trained neural network utilizing the ROI segmentation mask and a subset of the MR scout temporal frames with a temporal window size large enough to provide accurate estimation of the optimal TI frame for blood-pool and/or myocardium.

5. The computer-implemented method of claim 4, wherein the span of the MR scout temporal frames is within the temporal window size.

6. The computer-implemented method of claim 1, wherein utilizing the second trained neural network to determine the TI optimal TI frame comprises:

inputting, via the processing system, into the second trained neural network the span of the MR scout temporal frames and the ROI segmentation mask; and outputting, via the processing system, from the second trained neural network the optimal TI frame from the span of MR scout temporal frames.

7. The computer-implemented method of claim 1, wherein utilizing the second trained neural network to determine the optimal TI frame comprises predicting a score between 0 and 1 for each MR scout temporal frame within the span, wherein the score for the optimal TI frame is close to or at 1.

8. The computer-implemented method of claim 7, further comprising outputting, via the processing system, a user-perceptible indication when none of the MR scout temporal frames within the span have a respective score high enough to be considered the optimal TI frame.

9. The computer-implemented method of claim 1, wherein the series of MR scout temporal frames comprises 4-chamber views, 3-chamber views, 2-chamber views, axial views, long axial views, or short-axis views.

10. The computer-implemented method of claim 1, further comprising outputting, via the processing system, a user-perceptible indication of an optimal TI based on the optimal TI frame and a pulse sequence diagram of the TI-scout sequence.

11. A system for determining an optimal inversion time (TI), comprising:

a memory encoding processor-executable routines; and a processing system comprising one or more processors and configured to access the memory and to execute the processor-executable routines, wherein the processor-executable routines, when executed by the processing system, cause the processing system to:

obtain a series of magnetic resonance (MR) scout temporal frames of a subject from MR scout imaging data acquired with an MR scanner utilizing a TI-scout sequence;

obtain a TI-scout maximum intensity projection (MIP) image from the MR scout imaging data;

utilize a first trained neural network to localize a cardiac region in the TI-scout MIP image to generate a region of interest (ROI) segmentation mask for the cardiac region;

utilize the ROI segmentation mask on the TI-scout MIP image and the series of MR scout temporal frames to generate a ROI cropped TI-scout MIP image and ROI cropped MR scout temporal frames, respectively;

generate a distance score plot by computing a distance between each ROI cropped MR scout temporal frame and the ROI cropped TI-scout MIP image;

automatically analyze the distance score plot to approximate a span of the MR scout temporal frames for optimal TI frame estimation, wherein the span of the MR scout temporal frames encompasses a transition region comprising phase changes in the cardiac region including blood pool nulling, remote myocardium nulling, and initial recovery; and utilize a second trained neural network to determine an optimal TI frame from the span of the MR scout temporal frames, wherein determination of the optimal TI frame occurs in a single pass.

12. The system of claim 11, wherein the processor-executable routines, when executed by the processing system, further cause the processing system, prior to generating the distance score plot, to normalizing the ROI cropped TI-scout MIP image and the ROI cropped MR scout temporal frames.

13. The system of claim 12, wherein automatically analyzing the distance score plot to approximate the span of the MR scout temporal frames for optimal TI frame estimation comprises:

determining a point on the distance score plot having a maximum distance, wherein the point represents the transition region; and selecting a number of temporally consecutive frames from the series of MR scout temporal frames that both flank and include the transition region as the span of the MR scout temporal frames.

14. The system of claim 11, wherein utilizing the second trained neural network to determine the TI optimal TI frame comprises:

inputting, via the processing system, into the second trained neural network the span of the MR scout temporal frames and the ROI segmentation mask; and outputting, via the processing system, from the second trained neural network the optimal TI frame from the span of MR scout temporal frames.

15. The system of claim 11, wherein utilizing the second trained neural network to determine the optimal TI frame comprises predicting a score between 0 and 1 for each MR scout temporal frame within the span, wherein the score for the optimal TI frame is close to or at 1.

16. The system of claim 15, wherein the processor-executable routines, when executed by the processing system, further cause the processing system to output a user-perceptible indication when none of the MR scout temporal frames within the span have a respective score high enough to be considered the optimal TI frame.

17. The system of claim 11, wherein the series of MR scout temporal frames comprises 4-chamber views, 3-chamber views, 2-chamber views, axial views, long axial views, or short-axis views.

18. A non-transitory computer-readable medium, the computer-readable medium comprising processor-executable code that when executed by a processing system comprising one or more processors, causes the processing system to:

obtain a series of magnetic resonance (MR) scout temporal frames of a subject from MR scout imaging data acquired with an MR scanner utilizing a TI-scout sequence;

obtain a TI-scout maximum intensity projection (MIP) image from the MR scout imaging data;

utilize a first trained neural network to localize a cardiac region in the TI-scout MIP image to generate a region of interest (ROI) segmentation mask for the cardiac region;

utilize the ROI segmentation mask on the TI-scout MIP image and the series of MR scout temporal frames to generate a ROI cropped TI-scout MIP image and ROI cropped MR scout temporal frames, respectively;

generate a distance score plot by computing a distance between each ROI cropped MR scout temporal frame and the ROI cropped TI-scout MIP image;

automatically analyze the distance score plot to approximate a span of the MR scout temporal frames for optimal TI frame estimation, wherein the span of the MR scout temporal frames encompasses a transition region comprising phase changes in the cardiac region including blood pool nulling, remote myocardium nulling, and initial recovery; and utilize a second trained neural network to determine an optimal TI frame from the span of the MR scout temporal frames, wherein determination of the optimal TI frame occurs in a single pass.

19. The non-transitory computer-readable medium of claim 18, wherein automatically analyzing the distance score plot to approximate the span of the MR scout temporal frames for optimal TI frame estimation comprises:

determining a point on the distance score plot having a maximum distance, wherein the point represents the transition region; and selecting a number of temporally consecutive frames from the series of MR scout temporal frames that both flank and include the transition region as the span of the MR scout temporal frames.

20. The non-transitory computer-readable medium of claim 18, wherein utilizing the second trained neural network to determine the optimal TI frame comprises predicting a score between 0 and 1 for each MR scout temporal frame within the span, wherein the score for the optimal TI frame is close to or at 1.

* * * * *